United States Patent [19]

Heyl et al.

[11] Patent Number: 5,639,378

[45] Date of Patent: *Jun. 17, 1997

[54] METHOD FOR REMOVING COMPONENTS FROM SOLUTIONS

[75] Inventors: Barbara L. Heyl, Atlanta; Lynn C. Winterton, Roswell; Kai C. Su, Alpharetta; Jack C. White, Stone Mountain, all of Ga.

[73] Assignee: Ciba-Geigy Corporation, Ardsley, N.Y.

[*] Notice: The term of this patent shall not extend beyond the expiration date of Pat. No. 5,496,471.

[21] Appl. No.: 459,769

[22] Filed: Jun. 2, 1995

Related U.S. Application Data

[60] Division of Ser. No. 24,224, Mar. 1, 1993, Pat. No. 5,496,471, which is a continuation-in-part of Ser. No. 873,215, Apr. 24, 1992, abandoned, which is a continuation-in-part of Ser. No. 814,728, Dec. 19, 1991, abandoned, which is a division of Ser. No. 671,967, Mar. 18, 1991, Pat. No. 5,080,800, which is a division of Ser. No. 461,988, Jan. 8, 1990, Pat. No. 5,056,689.

[51] Int. Cl.⁶ .................................................. B01D 15/04
[52] U.S. Cl. ............................................. 210/681; 210/683
[58] Field of Search ............................... 210/681, 683, 210/685, 686

[56] References Cited

U.S. PATENT DOCUMENTS

| | | | |
|---|---|---|---|
| 2,061,958 | 11/1936 | Chapman | 215/37 |
| 2,160,602 | 5/1939 | Nagel | 65/45 |
| 2,761,833 | 9/1956 | Ward | 210/282 |
| 2,869,724 | 1/1959 | McDevitt | 210/282 |
| 3,038,610 | 6/1962 | Hetherington | 210/282 |
| 3,346,146 | 10/1967 | Thompson | 222/189 |
| 3,361,304 | 1/1968 | Thompson | 222/189 |
| 3,422,993 | 1/1969 | Boehm et al. | 222/190 |
| 3,449,081 | 6/1969 | Hughes | 210/282 |
| 3,622,049 | 11/1971 | Thompson | 222/190 |
| 3,760,987 | 9/1973 | Meterhoefer | 222/153 |
| 3,951,798 | 4/1976 | Haldoupoulos | 210/452 |
| 3,977,560 | 8/1976 | Stumpf et al. | 222/189 |
| 3,985,271 | 10/1976 | Gardner | 222/190 |
| 3,985,648 | 10/1976 | Casolo | 210/686 |
| 4,002,168 | 1/1977 | Petterson | 128/233 |
| 4,013,410 | 3/1977 | Thomas et al. | 21/58 |
| 4,018,364 | 4/1977 | Wright | 222/190 |
| 4,115,272 | 9/1978 | Mukhamedyarov et al. | 210/266 |
| 4,131,544 | 12/1978 | Nasik | 210/40 |
| 4,184,615 | 1/1980 | Wright | 222/190 |

(List continued on next page.)

FOREIGN PATENT DOCUMENTS

| | | |
|---|---|---|
| 427392 | 4/1938 | Belgium . |
| 0 366 534 | 5/1990 | European Pat. Off. . |
| 0 429 732 | 6/1991 | European Pat. Off. . |
| 0 439 999 | 8/1991 | European Pat. Off. . |
| 1227667 | 8/1960 | France . |
| 1 367 129 | 8/1964 | France . |
| 2 638 428 | 5/1990 | France . |
| U-8622273 | 7/1989 | Germany . |
| WO-A-82/00128 | 1/1982 | WIPO . |

*Primary Examiner*—Ivars Cintins
*Attorney, Agent, or Firm*—Wenderoth, Lind & Ponack

[57] ABSTRACT

A dispensing device having a container body defining a solution retaining chamber therein, the container having an outlet for dispensing the solution from the chamber and means for removing a component from the solution as the solution is dispensed from the chamber through the container outlet. A method is provided for administering to a patient a pharmacologically active substance which substance is stable only at a pH value which is extreme in the acidic or alkaline region and at which pH value the substance cannot be administered without causing discomfort and/or injury to the patient. The substance is maintained in a solution or dispersion at the pH at which it is stable until the time of administration. At this time the substance is administered through a chamber containing an ion exchange resin which changes the pH of the solution or dispersion to a value which will not cause discomfort and/or injury to the patient.

6 Claims, 6 Drawing Sheets

U.S. PATENT DOCUMENTS

| | | | |
|---|---|---|---|
| 4,231,872 | 11/1980 | Wolfgang | 210/93 |
| 4,250,141 | 2/1981 | Lehmann et al. | 422/44 |
| 4,259,184 | 3/1981 | D'Arnal | 210/85 |
| 4,276,160 | 6/1981 | Donnert et al. | 210/660 |
| 4,338,194 | 7/1982 | Tanny | 210/490 |
| 4,368,081 | 1/1983 | Hata et al. | 134/2 |
| 4,388,229 | 6/1983 | Fu | 252/549 |
| 4,396,583 | 8/1983 | LeBkoeuf | 422/301 |
| 4,463,880 | 8/1984 | Kramer et al. | 222/189 |
| 4,521,375 | 6/1985 | Houlsby | 422/29 |
| 4,529,511 | 7/1985 | Breeden et al. | 210/94 |
| 4,530,963 | 7/1985 | DeVoe et al. | 525/54.1 |
| 4,537,683 | 8/1985 | Isacoff et al. | 210/667 |
| 4,560,491 | 12/1985 | Sherman | 252/106 |
| 4,568,517 | 2/1986 | Kaspar et al. | 422/30 |
| 4,578,187 | 3/1986 | Alhäuser | 210/93 |
| 4,711,718 | 12/1987 | Nelson, Jr. | 210/282 |
| 4,714,550 | 12/1987 | Malson et al. | 210/244 |
| 4,721,624 | 1/1988 | Schumann | 426/286 |
| 4,747,954 | 5/1988 | Vaughn et al. | 210/670 |
| 4,756,710 | 7/1988 | Bondi et al. | 424/449 |
| 4,756,833 | 7/1988 | Schlossel | 210/662 |
| 4,758,351 | 7/1988 | Kern | 210/688 |
| 4,789,475 | 12/1988 | Harte et al. | 210/502.1 |
| 4,792,403 | 12/1988 | Togo et al. | 210/692 |
| 4,861,760 | 8/1989 | Mazuel et al. | 514/54 |
| 4,917,271 | 4/1990 | Kanner et al. | 239/327 |
| 5,013,459 | 5/1991 | Gettings | 210/282 |
| 5,056,689 | 10/1991 | Heyl et al. | 222/189 |
| 5,080,800 | 1/1992 | Heyl et al. | 210/679 |
| 5,496,471 | 3/1996 | Heyl et al. | 210/266 |

METHOD FOR REMOVING COMPONENTS FROM SOLUTIONS

This is a divisional application of Ser. No. 08/024,224, filed Mar. 1, 1993 (now U.S. Pat. No. 5,496,471), which is a continuation-in-part of now abandoned application Ser. No. 07/873,215, filed Apr. 24, 1992 which is a continuation-in-part of now abandoned application Ser. No. 814,728, filed Dec. 19, 1991, which application is a division of application Ser. No. 671,967, filed Mar. 18, 1991 (now U.S. Pat. No. 5,080,800), which is a division of application Ser. No. 461,988, filed Jan. 8, 1990 (now U.S. Pat. No. 5,056,689).

BACKGROUND OF THE INVENTION

The present invention relates to a solution dispenser and more particularly to a dispenser in which preservatives and other components may be removed from a solution as the solution is dispensed. The invention also provides a method for the removal of preservatives and other components from a solution as the solution is dispensed. In one embodiment, the invention provides a dispenser and method for altering the pH of a solution or dispersion as it passes through a dispenser.

Many solutions are available for making contact lenses more comfortable, safer, and easier to wear. For example, wetting solutions facilitate the wetting of a lens, soaking solutions serve as anti-microbial storage medium and prevent dehydration and distortion of the lens, and cleaning solutions remove accumulated eye secretions and other contaminants from lenses. A large number of other solutions are also used by contact lens patients. These ophthalmic solutions are typically marketed in squeezable plastic containers or aerosol cans having a nozzle through which the solution is dispensed.

Because these solutions come in contact either directly or indirectly with the eye, it is very important that they be free of microbial growth. To this end, it is common practice for preservatives to be provided in these solutions. Among the preservatives used in ophthalmic solutions are polymoxin B sulfate, quaternary ammonium compounds, chlorobutanol, organic mercurials, p-hydroxybenzoic acid esters, and certain phenyls and substituted alcohols.

A problem exists, however, in that the preservatives used in the ophthalmic solutions can cause eye irritation if used in high concentrations. For example, benzalkonium chloride (BAK) is used as a preservative in ophthalmic solutions and has broad anti-bacterial and anti-fungal activity when used with other components, such as disodium ethylene diamine-tetraacetic acid (EDTA). However, it has been reported that repeated use of BAK can denature the corneal protein and cause irreversible eye damage. Also, in addition to chemical sensitivity, a number of contact lens wearers have allergic reactions to the preservatives used in ophthalmic solutions, even at relatively low concentrations.

The typical remedy for overcoming chemical sensitivity and allergic reactions to preservatives in ophthalmic solutions entails switching the patients to an unpreserved solution. However, unpreserved solutions present problems in marketing, as well as in home storage, in that once the container housing the solution is opened, the solution quickly becomes contaminated and unsuitable for further use. They also tend to be very expensive to produce.

Therefore, there exists a need for an apparatus which removes preservatives, as well as other components, from a solution as the solution is dispensed to a patient.

There exists a further need for such an apparatus which is easily manufactured and economical to use.

There exists a further need for an apparatus which may be attached to a standard solution container.

SUMMARY OF THE INVENTION

The present invention relates to a device for removing a component, including but not limited to preservatives, from ophthalmic and other solutions as the solution is dispensed from a container. As employed herein the term "solution" is employed in a broad sense to include dispersions of one or more of the active components in a liquid to be dispensed from the container. The device preferably comprises a container having squeezable sidewalls defining a solution retaining chamber, but may also be an aerosol can or other container. The container also preferably includes a neck portion and a dispensing head having a container outlet on its end through which the solution is dispensed. Means for removing the component from the solution as the solution is dispensed from the chamber through the container outlet are also provided.

In a first embodiment, the means for removing a component from the solution comprises a scavenging material provided within the path of the solution as the solution is dispensed. In this embodiment, the device is a standard solution container housing a solution having the component to be removed, and the scavenging material is held within the dispensing head. The scavenging material may have a positive charge for scavenging negatively charged components or it may have a negative charge for scavenging positively charged components or it may be a material which selectively scavenges components by a size exclusion mechanism or it may comprise any other means for removing a component from solution.

In an alternative embodiment, a fitment may be utilized having a fitment body which is releasably engageable with a standard solution container. The fitment includes passage means within its body for allowing passing of the solution from the container to a fitment outlet. In this embodiment, the means for removing a component may comprise a scavenging material provided within the fitment so as to be within the path of the solution as the solution is dispensed from the container outlet to the fitment outlet. The fitment has the advantage of being able to be adapted to standard solution containers.

Also, means for providing a control of the flow of solution out of the container may be provided. For example, a check valve may be provided within the final dispensing outlet to prevent backflow of solution into the container following use. Additionally, means for regulating the flow of air into the container, namely, a second check valve, may be placed within the neck portion of a squeezable container for allowing air to flow into a depressed container, thereby restoring the container to its original shape. This embodiment will minimize the incidence of microbial growth in the area of the dispensing head proximate the final dispensing outlet.

Another embodiment of the present invention provides a dispensing device which is capable of holding an ophthalmic solution at a first pH and dispensing the solution at a different pH. The term "ophthalmic solution" as used herein is intended to mean any solution used in or around the eye, such as a pharmaceutical, eye wash, contact lens solution, or otherwise. The device includes a container body defining a solution retaining chamber therein for retaining the solution having the predetermined first pH and an outlet for dispensing the solution from the chamber; as well as means for changing the pH of the solution as the solution is dispensed from the chamber through the container outlet. Preferably, the pH changing means are in the form of an ionic exchange material provided within the path of the solution as the solution travels from the chamber to the container outlet. For example, the pH changing means may be an anionic exchange material for removing positively charged ions from the solution to raise the pH of the solution as the solution is dispensed from the chamber through the container outlet, or may be a cationic exchange material for removing negatively charged ions from the solution to lower the pH of the solution as the solution is dispensed from the chamber through the container outlet. As with the other embodiments of the present invention, the pH changing means may be an integral part of the container or may be a fitment capable of being attached to a standard, off-the-shelf container.

In respect to the pH changing aspect of this invention, it is noted that a large number of pharmacologically active substances are stable only at pH values which are extreme in the acidic or alkaline region. These substances cannot be administered at such extreme pH values without causing pain and/or injury to the recipient. This is true whether the administration is to the eye or another portion of the body of the recipient. However, due to the chemical nature of these substances, they must be maintained at these extreme pH values for storage stability. Many new drug candidates have been "shelved" as not commercially viable due to this problem even though their pharmacological activity is good.

The present invention provides a solution to this problem since it permits the substance to be stored in solution or dispersion at an extreme pH value in the acidic or alkaline range where it is stable until the time of its administration. At administration, the solution or dispersion containing the active substance is dispensed through a chamber containing the necessary ion exchange material to change the pH to a value which is acceptable to the patient and which will not cause pain and/or injury.

Thus, the invention provides a method for the administration of a pharmacologically active substance which substance is stable only at a pH value which is extreme in the acidic or alkaline region and at which pH value the substance cannot be administered without causing discomfort and/or injury to a patient, which comprises maintaining the substance in a solution or dispersion at the pH at which the substance is stable until the time of administration and administering the substance to the patient by passing the solution or dispersion containing the substance through a chamber containing an ion exchange material which changes the pH of the solution or dispersion to a value which will not cause discomfort and/or injury to the patient.

Therefore, it is an object of the present invention to provide an apparatus which removes preservatives, as well as other components, from a solution as the solution is dispensed to a patient.

It is also an object of the present invention to provide such an apparatus which is easily manufactured and economical to use.

It is also an object of the present invention to provide such an apparatus which may be adapted to a standard solution container.

It is a further object to provide an apparatus and method for storing a solution or dispersion at a given pH value at which a pharmacological substance contained therein is stable but which is not optimal for administration and subsequently administering the substance through a chamber which changes the pH of the solution or dispersion to a value which is acceptable for administration.

These and other objects and advantages will be more apparent from the following detailed description of the invention.

DETAILED DESCRIPTION OF THE INVENTION

Figure 5:
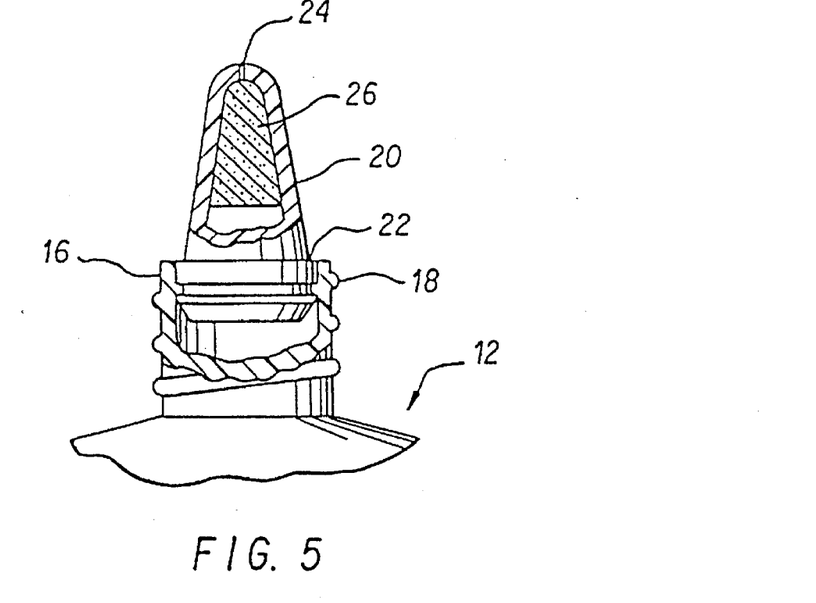
FIG. 5 is a partial cross-sectional view of an embodiment of the present invention in which the dispensing head is snap-fitted onto a container.
Figure 6:
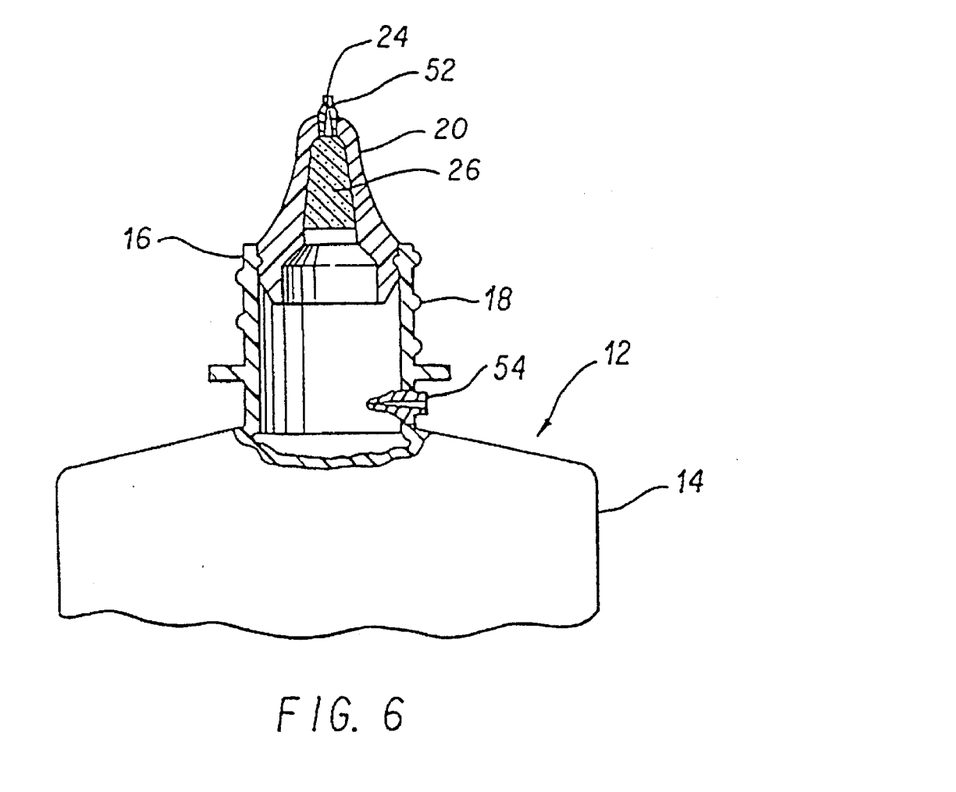
FIG. 6 is a partial cross-sectional view of an embodiment of the present invention having means for providing one-directional flow of solution out of a container.

Referring to the figures, a device 10 for removing components, such as preservatives, from solutions, such as an ophthalmic solution, is shown. The device 10 includes a container 12, preferably constructed of molded plastic, having resilient sidewalls 14 which define a solution retaining chamber and which preferably may be deformed by inward pressure to produce a pressure within the container 12 for using and dispensing its contents. The container 12 is provided with an upstanding neck portion 16 having external threads 18 thereabout. A dispensing head 20 is provided atop the neck portion 16, either integrally, as shown in FIGS. 1–4, by threading engagement, or by snap-fitting engagement as shown in FIGS. 5 and 6. A flange portion 22 is provided between the dispensing head 20 and the container neck 16. The dispensing head 20 has passage means, such as a duct or other passageway, through its length which in turn has a first end in communication with the chamber and a container outlet 24 at the other end.

Figure 1:
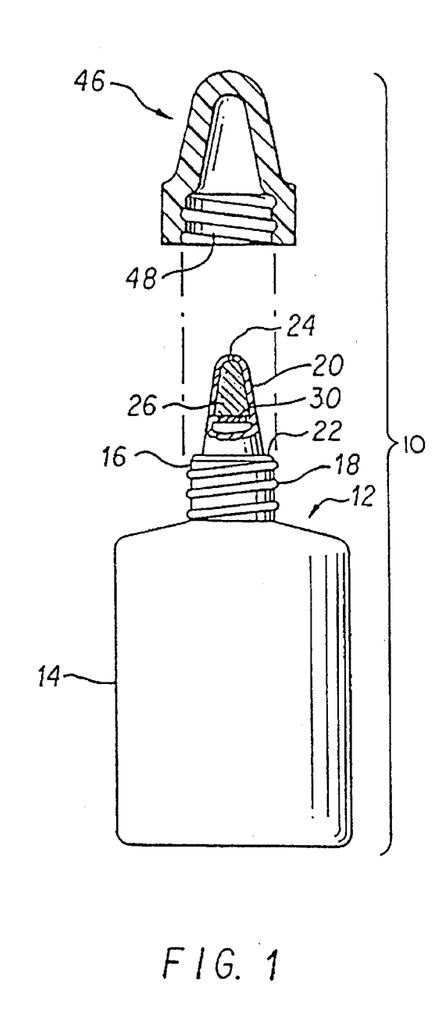
FIG. 1 is an exploded view of a first embodiment of the present invention in which scavenging material is provided within a container.
Figure 2:
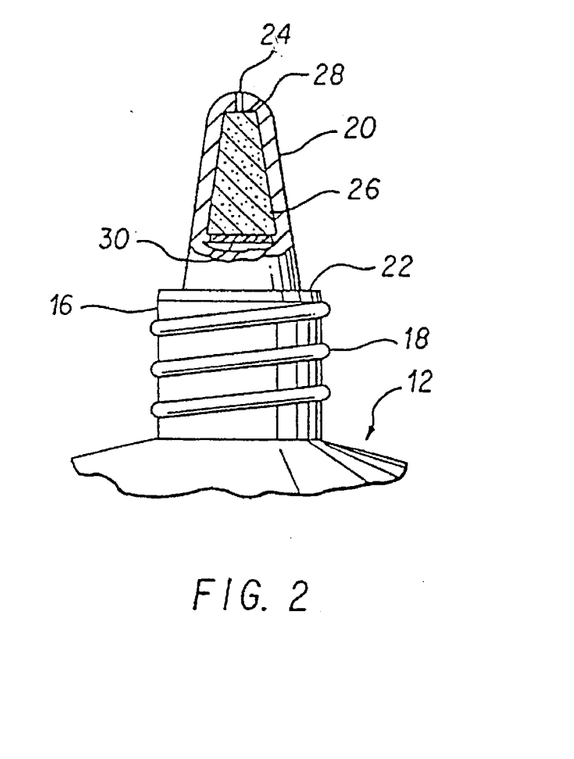
FIG. 2 is a partial cross-sectional view of a first embodiment of the present invention in which scavenging material is provided within a container.

In a first embodiment of the present invention, shown in FIGS. 1 and 2, means for removing preservatives or other components are placed directly within the dispenser head 20. In its preferred form, the preservative removing means comprise scavenging material 26 provided intermediate the chamber and the container outlet 24, so as to be within the path of the solution as the solution is dispensed from the container 12. The material 26 should be positioned as close as possible to the outlet 24 to minimize empty space in the upper portion of the dispensing head 20. The material 26 may be compressed into a porous mass which is preferably insert molded into the dispensing head 20. However, any other means of maintaining the material in the path of the solution may also be used. Alternatively, as shown in FIG. 2, the material 26 may be in the form of fine particles and held in place by porous supporting members 28 and 30. The members 28 and 30 may be made from porous plastic, such as porous polyethylene. In either case, it is important that the solution pass through the scavenging material 26 as it exits the container 12 so that the component is removed upon contact with the scavenging material 26.

Figure 3:
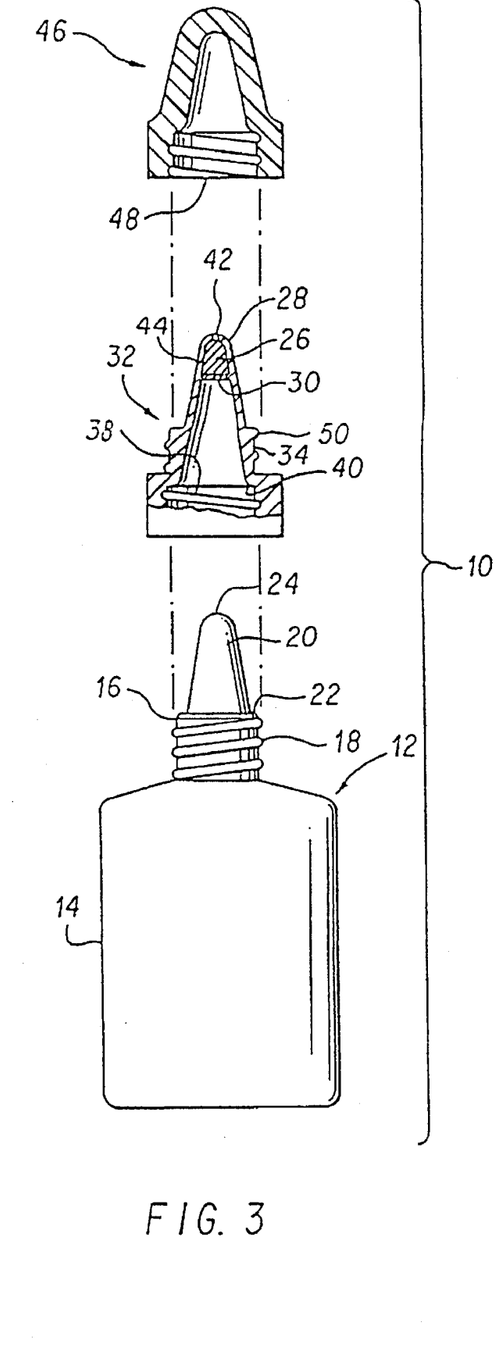
FIG. 3 is an exploded view of a second embodiment of the present invention in which scavenging material is provided within a fitment.
Figure 4:
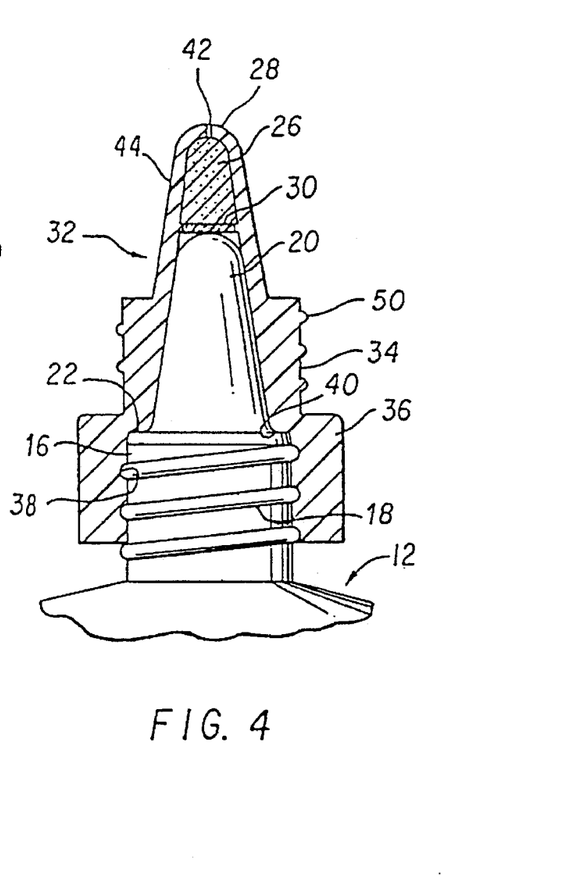
FIG. 4 is a partial cross-sectional view of a second embodiment of the present invention in which scavenging material is provided within a fitment.

A second embodiment of the invention, shown in FIGS. 3 and 4, includes a fitment 32 having a body 34 which is affixable to a standard-size container 12, such as described above but without the scavenging material 26 within its dispensing head 20. The lower portion 36 of the fitment 32 is provided with internal threads 38 which complimentarily mate with threads 18 on the outer surface of the neck portion 16 so that the fitment 32 may be releasably matable to the container 12. As seen in FIG. 4, when the fitment 32 is in threaded relationship with the container neck portion 16, an internal flange 40 of the fitment 32 rests atop the neck portion 16 to provide a seal between the fitment 32 and container 12. The fitment 32 has a fitment outlet 42 atop a tapered upper section 44, as well as a passage or duct through its length. The passage is preferably adjacent to and in flow registration with the container outlet 24 at one end and opens to the fitment outlet 42 at its other end. In this alternative embodiment, the scavenging material 26 is provided within the fitment 32, and removes the component, such as preservative, from the solution as the solution passes from the container outlet 24 to the fitment outlet 42. As in the first embodiment, the scavenger material 26 may be in solid mass or powder or other form.

FIG. 6 shows a device 10 of the present invention which includes means for providing one-directional flow of solution out of the container, such as a check valve 50. Preferably, the valve 50 is a deformable, polymeric valve that is positioned within the container outlet 24 so as to be in flow communication with the interior portion of the dispensing head 20 at one end and with the atmosphere at a second end. In its normal or closed position, the valve 50 does not allow air or solution to flow into or out of the container 12. However, as a result of the pressure exerted onto the container 12 during use, the valve moves to an open position that allows the solution to pass through to the atmosphere. When the pressure on the container 12 is stopped, the valve 50 closes and any solution remaining atop the valve 50 cannot be pulled back inside the container 12, thereby minimizing the incidence of organisms reentering the container 12 after use.

Also, when a squeezable container 12 is used, means for drawing air into the container 12 may be provided for returning the container 12 to its original shape. Preferably, a second one way check valve 54 is provided within the neck portion 16 and below the scavenging material 26. Upon release of the container 12 by the user, air is drawn into the container 12 by the valve 54, thereby restoring the container 12 to its proper shape. Also, because the valve 54 is one-directional, solution-from within the container 12 cannot leak out to the atmosphere through the valve 54. Furthermore, because the second valve 54 is below the scavenging material 26, any organism which should happen to be drawn from the air into the container will be deposited into the preserved solution and killed.

Both the dispensing head 20 of the first embodiment and the fitment 32 of the second embodiment may include a closure cap 46. The closure cap 46 may have internal threads 48 capable of matingly engaging with either the threads 18 of the neck portion 16, as shown in FIG. 1, or the external threads 50 of the fitment 32, as shown in FIG. 3, and resting on flange 22.

Of course, containers other than squeezable plastic types may be utilized. The scavenging material may be placed within an aerosol type dispenser, a solid bottle, or some other container.

Virtually any type of scavenging material 26 for removing a preservative or other component from solution may be used. For example, removal of benzalkonium chloride or other quaternary ammonium compounds can be accomplished by an ionic exchange mechanism or chemical affinity, for example, using fumed silica. The scavenging material 26 would preferably be an inert material with a negative charge, and the positively charged quaternary ammonium compound would adhere to the material 26 as it flows through the fitment 32 or dispensing head 20, depending on the embodiment. Examples of products capable of removing positively charged preservatives such as BAK include AG-50X-8, AG-50X-16, BIO-BS-SM2, and BIO REX70, all available from BIO-RAD Laboratories, Richmond, Calif. and Acropor 5A-6404 available from Gelman Sciences, Ann Arbor, Mich. Similarly, negatively charged components, such as acids, may be removed by using positively charged scavenging material 26. Examples of such scavenging material includes AG-1, AG-2XS, and AG-10 Alumina from BIO-RAD Laboratories. For example, it has been found that scavenging material 26 comprising Chelex 100 from BIO-RAD will remove Thimerosal from solution. Alternatively, the scavenging material may be porous plastic, such as porous polyethylene, imbedded with a cross-linked styrene divinyl benzene which is sulfonated to produce either a positively charged hydrogen form or a negatively charged sodium form. Other scavenging materials useful in the present invention are those relating to chemical affinity techniques, such as immunoassay, active site binding and affinity chromatography.

As one particular example, it has been found that a scavenging material comprised of a mixture of "Bio Rex 5" and "AG-4", both BIO-RAD products, in a 75 to 25 ratio will almost completely remove 0.1% sorbic acid from a solution and raise the pH of the solution from 4.0 to 7.0. This is important since sorbic acid is a commonly used preservative in contact lens solutions. In addition, sorbic acid is normally stored at pH=7.0, where it is not stable. At pH=4.0, it is very stable but cannot be instilled into the eye. The present invention will therefore allow solution to be stored at low pH and the pH raised to an ocularly acceptable level as the solution is administered.

Other preservatives that are not directly charged, such as chlorhexadine, could also be removed by the present invention. For example, a size exclusion mechanism may be utilized for removing certain types of preservative compounds. Overall, the term "scavenging material" as used herein refers to all material which will remove or change the nature of preservatives or other components in a solution exiting the container.

As examples of the ion-exchange resins which can be employed either in connection with the removal of preservative or pH change aspect of the present invention, there may be mentioned those which can safely be used in the treatment of food under conditions prescribed by the Food and Drug Administration. They are prepared in appropriate physical form and consist of one or more of the following:

(1) Sulfonated copolymer of styrene and divinylbenzene.
(2) Sulfonated anthracite coal meeting the requirements of ASTM-D388-38, Class I, Group 2.
(3) Sulfite-modified cross-linked phenol-formaldehyde, with modification resulting in sulfonic acid groups on side chains.
(4) Methacrylic acid-divinylbenzene copolymer.
(5) Cross-linked polystyrene, first chloromethylated then aminated with trimethylamine, dimethylamine, diethylenetriamine, or dimethylethanolamine.
(6) Diethylenetriamine, triethylenetetramine, or tetraethylenepentamine cross-linked with epichlorohydrin.
(7) Cross-linked phenol-formaldehyde activated with one or both of the following: Triethylene tetramine and tetraethylenepentamine.
(8) Reaction resin of formaldehyde, acetone, and tetraethylenepentamine.
(9) Completely hydrolyzed copolymers of methyl acrylate and divinylbenzene.
(10) Completely hydrolyzed terpolymers of methyl acrylate, divinylbenzene and acrylonitrile.
(11) Sulfonated terpolymers of styrene, divinylbenzene, and acrylonitrile or methyl acrylate.
(12) Methyl acrylate-divinylbenzene copolymer containing not less than 2 percent by weight of divinylbenzene, aminolyzed with dimethylaminopropylamine.
(13) Methyl acrylate-divinylbenzene copolymer containing not less than 3.5 percent by weight of divinylbenzene, aminolyzed with dimethylaminopropylamine.
(14) Epichlorohydrin cross-linked with ammonia.
(15) Sulfonated tetrapolymer of styrene, divinylbenzene, acrylonitrile, and methyl acrylate derived from a mixture of monomers containing not more than a total of 2 percent by weight of acrylonitrile and methyl acrylate.
(16) Methyl acrylate-divinylbenzene diethylene glycol divinyl ether terpolymer containing not less than 3.5 percent by weight of divinylbenzene and not more than 0.6 percent by weight of diethylene glycol divinyl ether, aminolyzed with dimethylaminopropylamine.
(17) Styrene-divinylbenzene cross-linked copolymer, first chloromethylated then aminated with dimethylamine and oxidized with hydrogen peroxide whereby the resin contains not more than 15 percent by weight of vinyl N,N-dimethylbenzylamine-N-oxide and not more than 6.5 percent by weight of nitrogen.

These are, of course, illustrative and not exhaustive of those ion exchange resins which can be employed. It is also apparent that the particular ion exchange resin to be employed will vary with the particular formulation which is to be passed through it in order to obtain optimal results.

To further illustrate the ion exchange resins for use in the invention the following exemplary information is set forth. The following listed resins were obtained from Rohm & Haas Company:

Carboxyl Resins
Amberlite® IRC-76
Modified acrylic polymers in the $H^+$ form
Amberlite® IRC-50
Divinylbenzene/methacrylic acid copolymer in the $H^+$ form
Dualite® C-433
Sulfonic Resins
Ambersep® 252 H Resin
Sulfonated divinylbenzene/styrene copolymer in the $H^+$ form
Amberlite® IR-120(H) –20+40 Resin
Sulfonated divinylbenzen/styrene copolymer in the $H^+$ form Each of the resins was received in the $H^+$ form and, in the following described manner, each was converted to the $Na^+$ form. 30 Grams of the resin was placed in a column and 1.5 liters of 4% NaOH was passed through the column. Ultra pure $H_2O$ was then passed through the column until a constant $pK_b$ was reached.

| Resin | $pk_b$ |
| --- | --- |
| Carboxyl | |
| Amberlite ® IRC-76 | –9.8 |
| Amberlite ® IRC-50 | –9.9 |
| Dualite ® C-433 | –9.7 |
| Sulfonated | |
| Ambersep ® 252 | –9.5 |
| Amberlite ® IR-120 | –9.6 |

Each of these resins proved to be particularly suitable for incorporation in a device as shown in FIGS. 7 through 10 which is capable of holding an ophthalmic solution at a first pH and dispensing the solution at a different pH.

Various pharmacological agents such as drugs, diagnostic agents, ocular lubricants and the like can be administered in accordance with the invention. As examples, the following can be mentioned:

Antibacterial substances such as beta-lactam antibiotics, such as cefoxitin, ciprofloxacin, n-formamidoylthienamycin and other thienamycin derivatives, tetracyclines, chloramphenicol, neomycin, carbenicillin, colistin, penicillin G, polymyxin B, vancomycin, cefazolin, cephaloridine, chibrorifamycin, gramicidin, bacitracin and sulfonamides:

Aminoglycoside antibiotics such as gentamycin, kanamycin, amikacin, sisomicin and tobramaycin;

Naiidixic acid and its analogs such as norfloxacin and the antimicrobial combination fluoroalanine/pentizidone, nitrofurazones and analogs thereof;

Antihistaminics and decongestants such as pyrilamine, chlorpheniramine, tetrahydrazoline, antazoline and analogs thereof;

Anti-inflammatories such as diclofenac, ketorolac, cortisone, hydrocortisone, hydrocortisone acetate, betamethasone, dexamethasone, dexamethasone sodium phosphate, prednisone, methylprednisolone, medrysone, fluorometholone, prednisolone, prednisolone sodium phosphate, triamcinolone, indomethacin, suiindac, its salts and its corresponding sulfides, and analogs thereof;

Miotics and anticholinergics such as echothiophate, pilocarpine, physostigmine salicylate, diisopropylfluorophosphate, epinephrine, dipivaloylepinephrine, neostigmine, echothiopate iodide, demecarium bromide, carbamoyl choline chloride, methacholine, bethanechol, and analogs thereof;

Most cell stabilizers such as cromolyn sodium;

Mydriatics such as atropine, homatropine, scopolamine, hydroxyamphetamine, ephedrine, cocaine, tropicamide, phenylephrine, cyclopentolate, oxyphenonium, eucatropine, and analogs thereof;

Other drugs used in the treatment of conditions and lesions of the eyes such as:

Antiglaucoma drugs for example timolol, and especially its maleic salt and R-timolol and a combination of timolol or R-timolol with pilocarpine, as well as many other adrenergic agonists and/or antigonists; epinephrine and an epinephrine complex, or prodrugs such as bitartrate, borate, hydrochloride and dipivefrine derivatives and hyperosmotic agents such as glycerol, mannitol and urea: carbonic anhydrase inhibitors such as acetazolamide, dichlorphenamide, 2-(p-hydroxyphenyl)-thio-5-thiophenesulfonamide, 6-hydroxy-2-benzothiazolesulfonamide; and 6-pivaloyloxy-2-benzothiazolesulfonamide;

Antiparasitic compounds and/or anti-protozoal compounds such as ivermectin, pyrimethamine, trisulfapidimidine, clindamycin and corticosteroid preparations;

Compounds having antiviral activity such as acyclovir, 5-iodo-2'-deoxyuridine (IDU), adenosine arabinoside (Ara-A), trifluorothymidine, and interferon and interferon-inducing agents such as poly I:C;

Antifungal agents such as amphotericin B, nystatin, flucytosine, natamycin and miconazole;

Anesthetic agents such as etidocaine cocaine, benoxinate dibucaine hydrochloride, dyclonine hydrochloride, naepaine, phenacaine hydrochloride, piperocaine, proparacaine hydrochloride, tetracaine hydrochloride, hexylcaine, bupivacaine, lidocaine, mepivacaine and prilocaine;

Ophthalmic diagnostic agents, such as:
  (a) those used to examine the retina such as sodium fluorescein;
  (b) those used to examine the conjunctiva, cornea and lacrimal apparatus, such as fluorescein and rose bengal; and
  (c) those used to examine abnormal pupillary responses such as methacholine, cocaine, adrenaline, atropine, hydroxyamphetamine and pilocarpine;

Ophthalmic agents used as adjuncts in surgery, such as alpha-chymotrypsin and hyaluronidase;

Chelating agents such as ethylenediaminetetraacetic acid (EDTA) and deferoxamine;

Immunosuppressants and anti-metabolites such as methotrexate, cyclophosphamide, 6-mercaptopurine and azathioprine; and combinations of the compounds mentioned above, such as antibiotics/antiinflammatories combinations such as the combination of neomycin sulfate and dexamethasone sodium phosphate, and combinations concomitantly treating glaucoma, for example a combination of timolol maleate and aceclidine.

The foregoing agents will be principally used in the embodiment of the invention where a preservative agent is removed from a solution containing the agent as the solution is passed through the chamber containing the "scavenging material". However, in those cases where these agents must be stored at an extreme pH—either acidic or alkaline—in order to be stable, they may be administered in accordance with the pH change aspect of the invention.

Particular examples of drugs which are suitable for administration according to the pH change aspect of the invention are the antibacterial agent tosufloxacin (stable at pH 11), the cholinergic agent pilocarpine hydrochloride (stable at pH 4.5), the antibacterial agent tobramycin (stable at pH 8) and diveprin hydrochloride (stable at pH 2–3).

Referring to FIGS. 7 through 10, a dispensing device 110 which is capable of holding an ophthalmic solution at a first pH and dispensing the solution at a different pH is provided. The device 110 includes a container 112, preferably constructed of molded plastic, having resilient walls 114 which define a solution retaining chamber and which preferably may be deformed by inward pressure to produce a pressure within the container 112 for using and dispensing its contents. Of course, containers other than squeezable plastic types may be used, such as aerosol type dispensers or solid bottles. The container 112 is provided with an upstanding neck portion 116 having external threads 118 thereabout. A dispensing head 120 is provided atop the neck portion 116, either integrally, by threading engagement or by snapfitting. The dispensing head 120 has passage means extending through its length, the passage means having a first end in communication with the chamber and a second end being the dispensing outlet 126. A cap 122 having threads 124 engageable with threads 118 may be provided for closing the container 112.

Figure 8:
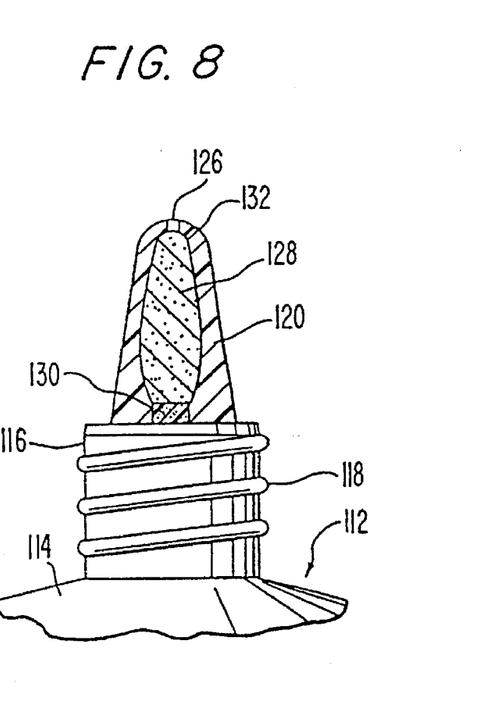
FIG. 8 is a partial cross-sectional view of the present invention in which ionic exchange material is provided within the container.

Means for changing the pH of the solution as the solution is dispensed from the chamber through the outlet 126 are provided. Preferably the pH changing means comprise an ionic exchange material 128 provided within the path of the solution as the solution travels from the chamber to the outlet 126. For example, as seen in FIG. 8, the ionic exchange material 128 may be located within the passage means of the dispensing head 120. Means for maintaining the ionic exchange material 128 in position within the passage means may also be provided. Such position maintaining means may be a first supporting member 130 located over the first end of the passage means and a second supporting member 132 located over the second end of the passage means. The ionic exchange material 128 will be held in position between the first and second supporting members 130 and 132, respectively. The supporting members 130 and 132 may be made from porous plastic, such as porous, non-woven polyethylene or polypropylene, or some other material which is permeable to the solution but which is impermeable to the ionic exchange material 128.

The type of ionic exchange material 128 used depends upon the characteristics of the solution to be dispensed and the desired pH change. For example, the ionic exchange material 128 is preferably an anionic exchange material capable of removing positively charged ions from the solution when it is desired to raise the pH of the solution as the solution is dispensed from the chamber through the outlet 126. Alternatively, the ionic exchange material 128 may be a cationic exchange material for removing negatively charged ions from the solution when it is desired to lower the pH of the solution as the solution is dispensed from the chamber through the outlet 126. The ionic exchange material 128 may be in the form of a powder, shavings, beads or otherwise so long as the solution can pass through as it is dispensed from the container 112. The amount of ionic exchange material 128 used depends upon a number of factors, including the length and diameter of the passage means, the hydrogen ion concentration of the solution, and the residence time of the solution in contact with the ionic exchange material 128. Overall, the length and diameter of the passage means must be enough to provide sufficient residence time for the hydrogen ion concentration of the solution to be changed to the desired final pH.

Figure 9:
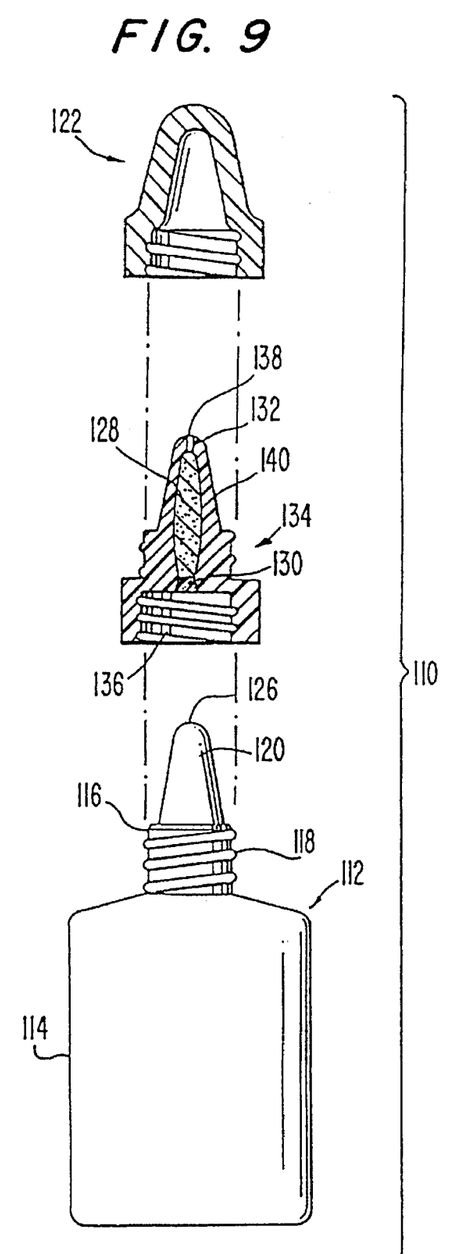
FIG. 9 is an exploded view of the present invention in which the ionic exchange material is provided in a fitment.
Figure 10:
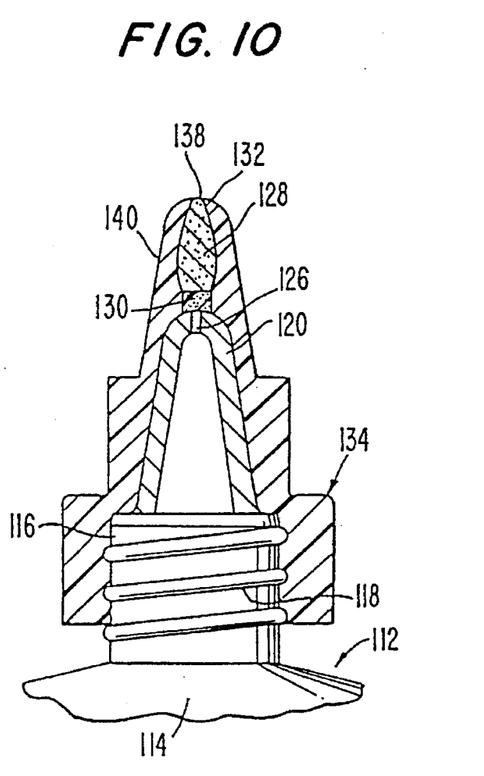
FIG. 10 is a partial cross-sectional view of the present invention in which the ionic exchange material is provided in a fitment.

Another embodiment of the device 110 of the present invention, shown in FIGS. 9 and 10, includes a fitment 134 which is affixable to a standard-size, off-the-shelf container 112, such as described above but without the ionic exchange material 128 within its dispensing head 120. The lower portion of the fitment 134 is provided with internal threads 136 which complimentarily mate with the threads 118 on the outer surface of the neck portion 116 so that the fitment 134 may be releasably matable to the container 112. As seen in FIG. 10, when the fitment 134 is in threaded relationship with the container neck portion 116, a seal is provided between the fitment 134 and the container 112. The fitment 134 has a dispensing outlet 138 atop a tapered upper section 140, as well as a passage or duct through its length. The passage is preferably adjacent to and in flow registration with the standard container outlet 126 at one end and opens to the dispensing outlet 138 at its other end. The ionic exchange material 128, as described above and preferably held in place by position maintaining means 130 and 132, is provided within the fitment 134, and changes the pH of the solution as the solution passes from the container outlet 126 to the dispensing outlet 138.

The following example is illustrative of a specific type of device which can be made according to the above description, but should not be viewed as limiting any aspect of the invention.

Pilocarpine hydrochloride; chemical name 2 (3H)-furanone, 3-ethyldihydro-4-[(1-methyl-1H-imidazol-5-yl)methyl]-, monohydrochloride, (3S-cis)-; is a well known direct acting cholinergic (parasympatomimetic) agent causing the pupillary constriction and reduction of intraocular pressure. It is commonly dispensed in a buffered ophthalmic solution which may consist of boric acid, potassium chloride, hydroxypropyl methylcellulose, sodium, carbonate, EDTA, purified water, and preserved with benzalkonium chloride. A problem exists, however, in that the pilocarpine hydrochloride solution is formulated at a pH of about 4.5 in order for it to remain stable in solution, and such pH is ocularly uncomfortable or otherwise incompatible. The device 110 of FIGS. 7 and 8 may be used to solve this problem by allowing the solution to be maintained at a stabilizing pH of about 4.5 while in the retaining chamber of the container 112, yet being at an ocularly acceptable pH of about 6.5 to 7.0 upon exiting the outlet 126.

Figure 7:
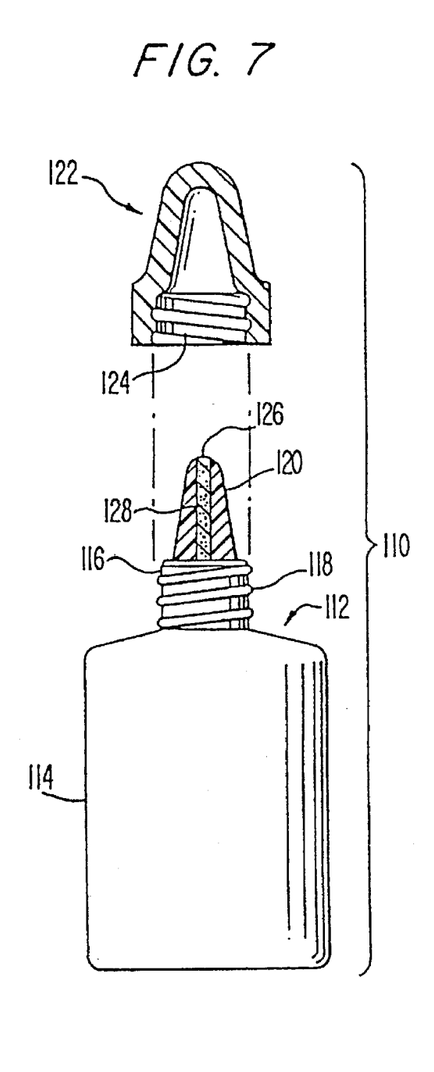
FIG. 7 is an exploded view of the present invention in which ionic exchange material is provided within the container.

Since it is desired to raise the pH of the pilocarpine hydrochloride solution from a relatively low pH of about 4.5 to an ocularly acceptable pH of about 6.8, the ionic exchange material 128 is preferably an anionic exchange material capable of removing positively charged ions from the solution. One such anionic exchange material is Amberlite® IRA-68 (available from Rohm & Haas Company, Philadelphia, Pa., 19105), which is a gel type, weakly basic anion exchange resin possessing tertiary amine functionality in a crosslinked acrylic matrix. Other such material is BIO-RAD® AG4 and BIO-RAD® AG3, both from BIO-RAD Laboratories. The Amberlite® IRA-68 material is available in uniform, spherical particles which can be easily placed within the passage means of the dispensing head 120 and held in position by porous supporting members 130 and 132. It should be noted that because the Amberlite® IRA-68 material attracts acids, it may be necessary to extract the free bases out of the resin material before placing the Amberlite® IRA-68 into the dispensing head 120. Failure to do so may result in an unwanted rise in pH of the solution. This can be accomplished by washing the resin in isopropyl alcohol or methanol (i.e., 1 liter of isopropyl alcohol for each 100 grams of Amberlite® IRA-68), followed by washing with sufficient purified water to remove any residual alcohols. It should also be noted that the Amberlite® IRA-68 material may swell upon wetting and shrink upon subsequent drying. Therefore, change of the material size must be accounted for when filling the dispensing head 120. Means for compensating for changes in size of the ionic exchange material 128 during the dispensing of the solution may be provided. For example, the first supporting member 130 may be constructed of a deformable sponge-like material capable of occupying the space created during expansion of the Amberlite® IRA-68 material.

Additionally, it should be clear that the fitment 134, as illustrated in FIGS. 9 and 10, may also be used to change the pH of the pilocarpine hydrochloride. In such an instance, a fitment 134 having Amberlite® IRA-68 material is placed atop a standard, off-the-shelf container of stabilized, pH 4.5 pilocarpine hydrochloride solution. Upon dispensing, the solution exits outlet 126 and travels through the passage means of the fitment 134, where it contacts the Amberlite® IRA-68 material. The Amberlite® IRA-68 material removes a sufficient number of hydrogen ions from the solution so that the solution has a pH of about 6.8 upon exiting the dispensing outlet 138.

Figure 11:
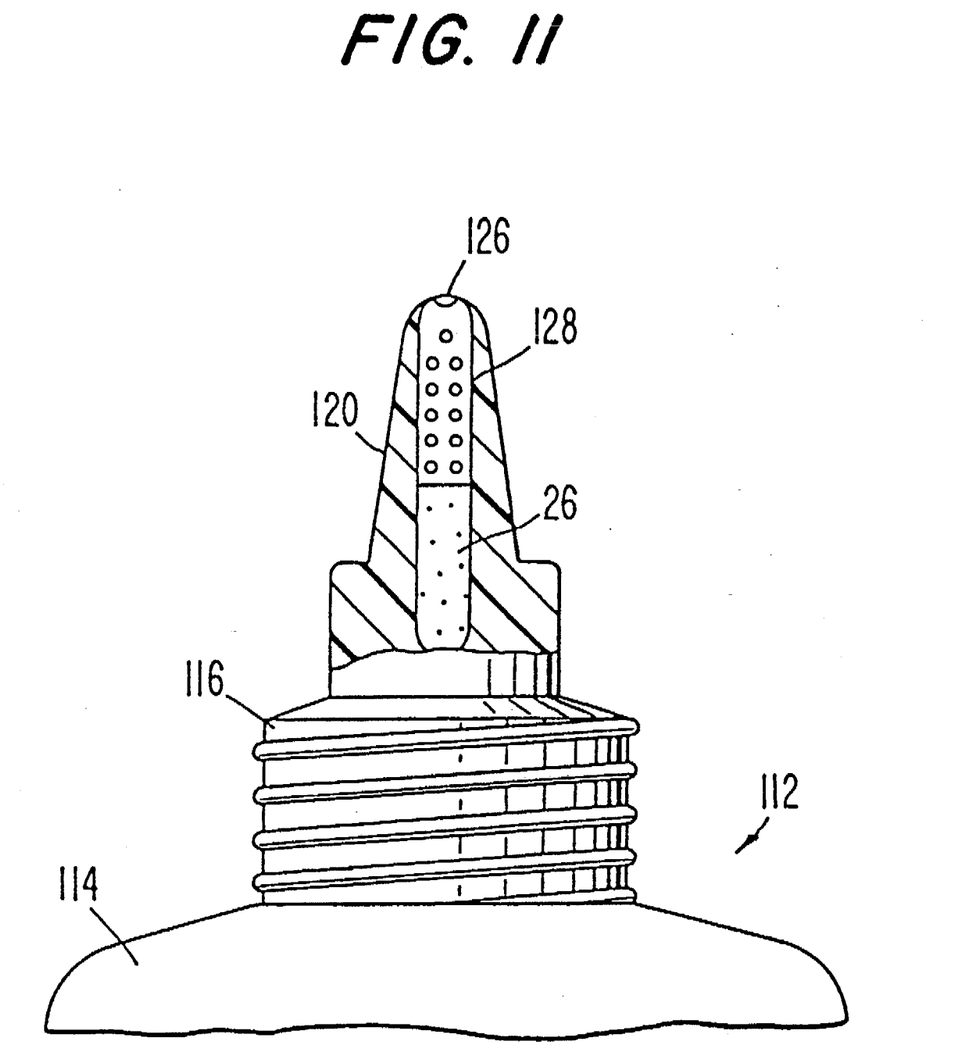
FIG. 11 is a partial cross-sectional view of the present invention in which scavenging material and ionic exchange material are provided in the container.

Also, the means for removing a component from the solution as the solution is dispensed from the chamber through the container outlet, as previously described herein, may be combined in the same container or fitment with the means for changing the pH of the solution as the solution is dispensed from the chamber through the container outlet, as described directly above. In such a device, illustrated in FIG. 11, the scavenging material 26 and the ionic exchange material 128 may both be placed within the passage means. For example, in the case of the above described typical pilocarpine hydrochloride solution, the scavenging material 26 would remove the benzalkonium chloride from the solution and the ionic exchange material 134 would raise the pH from about 4.5 to about 6.8. The resulting solution would therefore be preservative-free and ocularly compatible.

From the foregoing description of the invention, it should be seen that the present invention provides the ability to dispense preservative-free solutions from containers housing solutions that are preserved. Whereas the present invention has been described with respect to specific embodiments thereof, it should be understood that various changes and modifications will be suggested to one skilled in the art and it is intended that the invention encompass such changes and modifications that will fall within the scope of the appended claims.

What is claimed is:

1. A method for changing the pH of an ophthalmic solution containing a pharmacologically active substance which comprises bringing said ophthalmic solution having a first pH into contact with an ionic exchange material which removes an acid or base from the solution to obtain a solution having a second pH different from the first pH.

2. The method of claim 1, wherein the ionic exchange material is an anionic exchange material for removing positively charged ions from the solution to raise the pH of the solution as the solution is dispensed from the retaining chamber of a container through a dispensing outlet.

3. The method of claim 1, wherein the ionic exchange material is a cationic exchange material for removing negatively charged ions from the solution to lower the pH of the solution as the solution is dispensed from the retaining chamber of a container through a dispensing outlet.

4. The method of claim 1, wherein the said ophthalmic solution is stabilized at a first pH while stored in a container, and dispensed at a second pH after contacting the ionic exchange material.

5. The method of claim 1, wherein the ophthalmic solution is pilocarpine hydrochloride solution.

6. The method of claim 1, wherein the ophthalmic solution is pilocarpine hydrochloride solution and the ionic exchange material is a gel type weakly basic anion exchange resin possessing tertiary amine functionality in a crosslinked acrylic matrix.

* * * * *